United States Patent
Kim et al.

(10) Patent No.: US 12,285,395 B2
(45) Date of Patent: Apr. 29, 2025

(54) PHARMACEUTICAL COMPOSITION FOR PREVENTING OR TREATING ALLODYNIA CAUSED BY ANTICANCER AGENTS

(71) Applicant: UNIVERSITY-INDUSTRY COOPERATION GROUP OF KYUNG HEE UNIVERSITY, Gyeonggi-do (KR)

(72) Inventors: Sun Kwang Kim, Seoul (KR); Zee Hwan Lee, Seoul (KR); Dae Sik Jang, Seoul (KR); Woojin Kim, Seoul (KR); Kyung Jin Lee, Seoul (KR)

(73) Assignee: University-Industry Cooperation Group of Kyung Hee University, Gyeonggi-Do (KR)

( * ) Notice: Subject to any disclaimer, the term of this patent is extended or adjusted under 35 U.S.C. 154(b) by 1178 days.

(21) Appl. No.: 16/972,526

(22) PCT Filed: Jun. 7, 2019

(86) PCT No.: PCT/KR2019/006887
§ 371 (c)(1),
(2) Date: Dec. 4, 2020

(87) PCT Pub. No.: WO2019/235882
PCT Pub. Date: Dec. 12, 2019

(65) Prior Publication Data
US 2021/0267921 A1 Sep. 2, 2021

(30) Foreign Application Priority Data
Jun. 7, 2018 (KR) .......................... 1020180065562

(51) Int. Cl.
*A61K 31/192* (2006.01)
*A61K 36/54* (2006.01)
*A61P 25/02* (2006.01)
*A61P 25/04* (2006.01)

(52) U.S. Cl.
CPC ............ *A61K 31/192* (2013.01); *A61K 36/54* (2013.01); *A61P 25/02* (2018.01); *A61P 25/04* (2018.01); *A61K 2236/331* (2013.01); *A61K 2236/37* (2013.01)

(58) Field of Classification Search
None
See application file for complete search history.

(56) References Cited

U.S. PATENT DOCUMENTS 9,005,678 B1   4/2015   Cao et al.
2016/0113988 A1   4/2016   Ryu et al.

FOREIGN PATENT DOCUMENTS

| CN | 1303671 A | 7/2001 | |
|---|---|---|---|
| CN | 1312070 A | 9/2001 | |
| CN | 102666465 A | 9/2012 | |
| EP | 2330094 A1 | 6/2011 | |
| WO | WO-2012105476 A1 * | 8/2012 | ............. A61K 31/23 |

OTHER PUBLICATIONS

Liu et al. (Prevention of Paclitaxel Induced allodynia by minocycline: effect of loss of peripheral nerve fibers and infiltration of Macrophages in Rates, Molecular Pain, vol. 6, Jan. 2010). (Year: 2010).*
Bahar et al. (Herbal Medicine Goshajinkkigan Prevents Paclitaxel-Induced Mechanical Allodynia without Impairing Antitumor Activity of Paclitaxel, Evidenced-Based Complementary and Alternative Medicine, vol. 2013). (Year: 2013).*
Kim et al. (The Suppressive Effects of Cinnamomi Cortex and its Phytocompound Coumarin on Oxaliplatin-Induced Neuropathic Cold Allodynia in Rats, Molecules 2016, 21, 1253) (Year: 2016).*
Ahn et al., "Gyejigachulbu-Tang Relieves Oxaliplatin-Induced Neuropathic Cold and Mechanical Hypersensitivity in Rats via the Suppression of Spinal Glial Activation," Evidence-Based Complementary and Alternative Medicine, vol. 2014, article 436482, 2014.
Bahar et al., "Herbal Medicine Goshajinkigan Prevents Paclitaxel-Induced Mechnical Allodynia without Impairing Antitumor Activity of Paclitaxel," Evidence-Based Complementary and Alternative Medicine, vol. 2013, article ID 849754, 2013.
Chae et al., "Phytochemicals of Cinnamomi Cortex: Cinnamic Acid, but not Cinnamaldehyde, Attenuates Oxaliplatin-Induced Cold and Mechnical Hypersensitivity in Rats," Nutrients, 11(2):432, Feb. 19, 2019.
Cheng et al., "Herbal Medicine AC591 Prevents Oxaliplatin-Induced Peripheral Neuropathy in Animal Model and Cancer Patients," Front. Pharmacol., 8:344, Jun. 2017.
Kim et al., "The Suppressive Effects of Cinnamomi Cortex and Its Phytocompound Coumarin on Oxaliplatin-Induced Neuropathic Cold Allodynia in Rats," Molecules, vol. 21, No. 9, Article No. 1253, 2016.
Lee et al., "Cinnamomi cortex suppresses Oxaliplatin-induced neuropathic pain in rats via spinal glia modulation," Thesis of the Degree of Master of Science, Department of Science in Korean Medicine. Graduate School, Kyung Hee Jiversity, pp. 1-52, Feb. 2017.
Liu et al., "Cinnamic Acid: a Natural Product With Potential Use in Cancer Intervention," Int. J. Cancer, Feb. 16, 1995, 62:345-350.
Notice of Allowance, Application No. 9-5-2021-088846216, Korean Patent Office, Nov. 11, 2021.

(Continued)

*Primary Examiner* — Melissa S Mercier
(74) *Attorney, Agent, or Firm* — Gavrilovich, Dodd & Lindsey LLP

(57) ABSTRACT

The present disclosure relates to a composition for preventing, alleviating, or treating allodynia caused by anticancer agents, containing cinnamic acid or a pharmaceutically acceptable salt thereof as an active ingredient. The composition of the present disclosure can prevent, alleviate, or treat allodynia by being administered to a subject scheduled to receive anticancer agents or having received anticancer agents.

9 Claims, 8 Drawing Sheets

(56) References Cited

OTHER PUBLICATIONS

Lee et al., "Analysis of Cinnamic Acid, Cinnamaldehyde and 2-Methoxycinnamaldehyde in Cinnamomi Ramulus on the Market in Seoul by HPLC", Yakhak Hoeji, Aug. 31, 2013, 57(4):225-240.
Office Action, Korean Intellectual Property Office, Application No. 9-5-2023-006348800, Jan. 18, 2023.
Database GNPD [Online] MINTEL; Oct. 14, 2014, anonymous: "Chocolate Letter Shaped Cereal", XP055881875, Database Accession No. 2722449.
Database GNPD [Online] MINTEL; Mar. 7, 2017, anonymous: "Medicinal Herb Based Dietary Supplement", XP055881885, Database Accession No. 4661363.
De La Tour, Camille, European Search Report, Application No. 19815461.9, European Patent Office, Feb. 14, 2022.
Chae et al., "Phtochemicals of Cinnamomi Cortex: Cinnamic Acid, but not Cinnamaledhyde, Attenuates Oxaliplatin-Induced Cold and Mechnical Hypersensitivity in Rates," Nutrients, 11:432, Feb. 19, 2019.
Kim et al., "Supplementary Materiasl: Suppressive Effects of Cinnamomi Cortex and Its Phytocompound Coumarin on Oxaliplatin-Induced Neuropathic Cold Allodynia in Rats," Molecules, 21:1253, 2016.

* cited by examiner

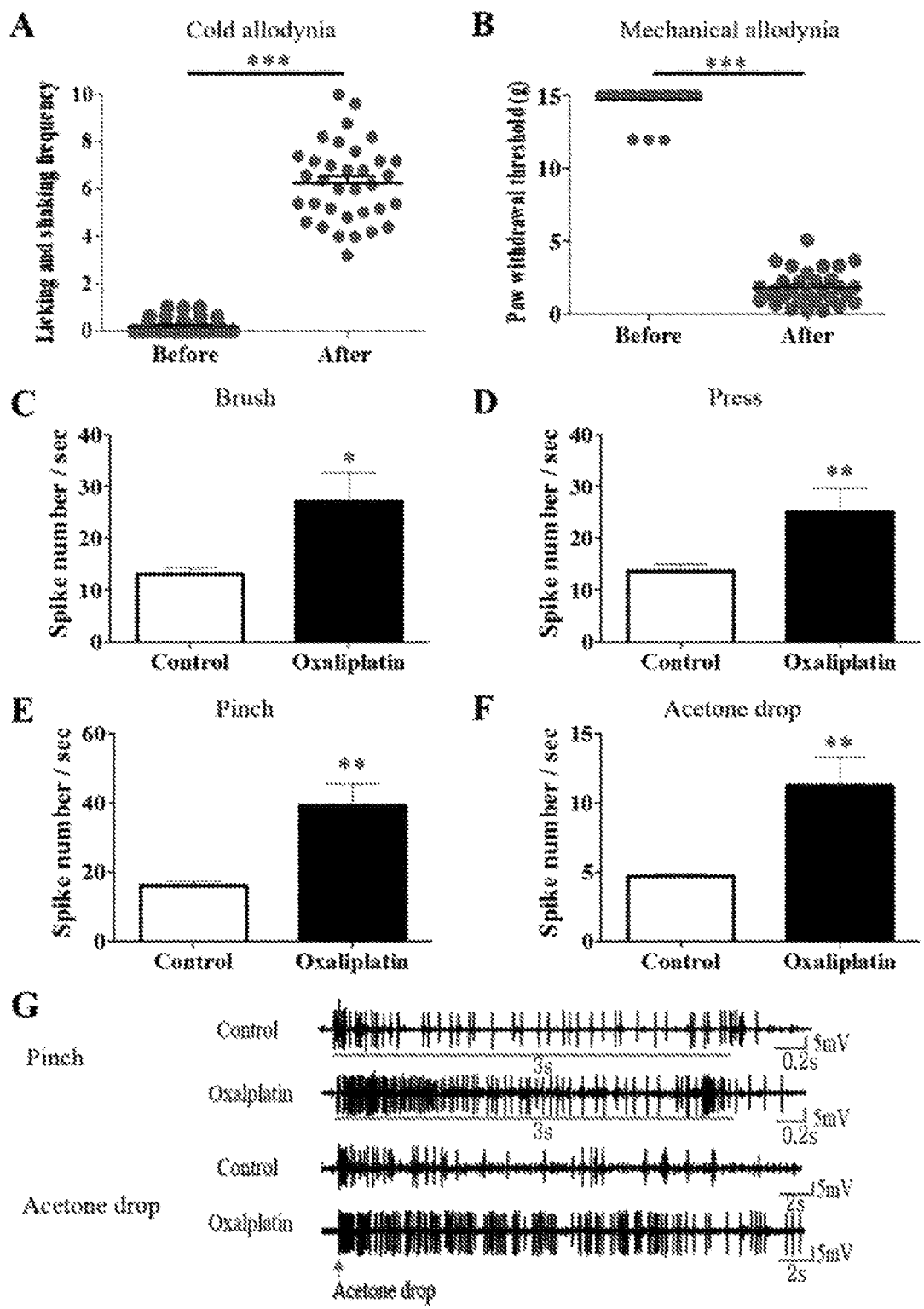
FIG. 4A-G

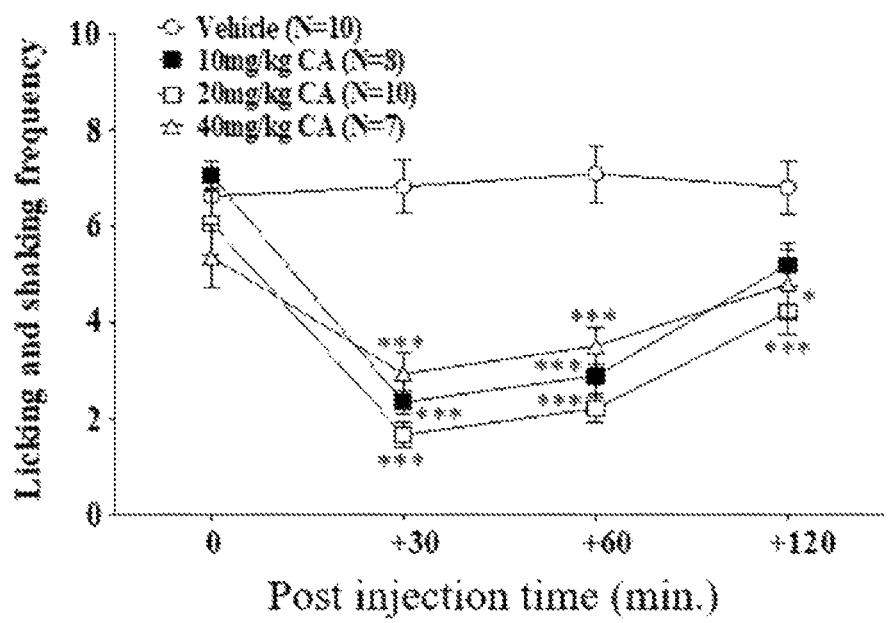
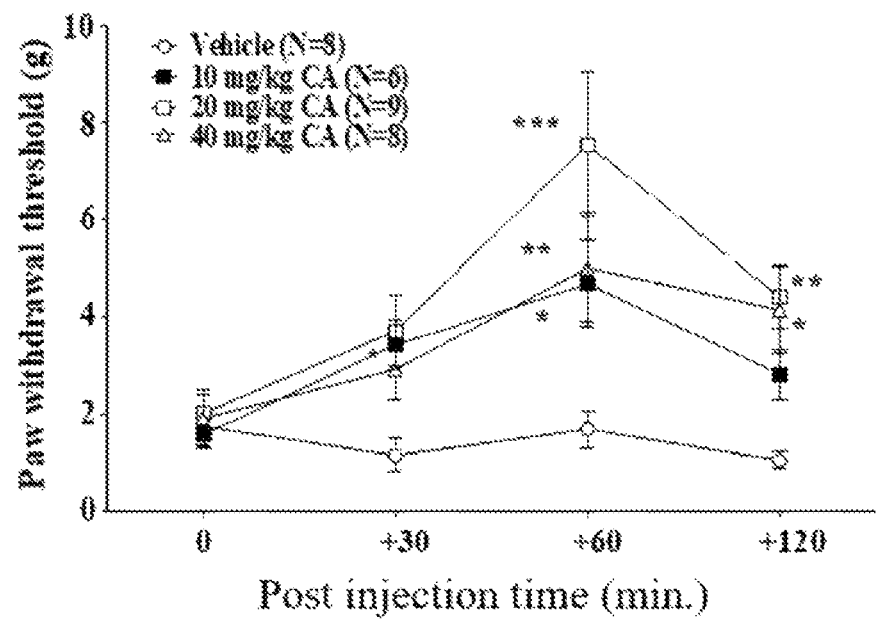
FIG. 5A-B

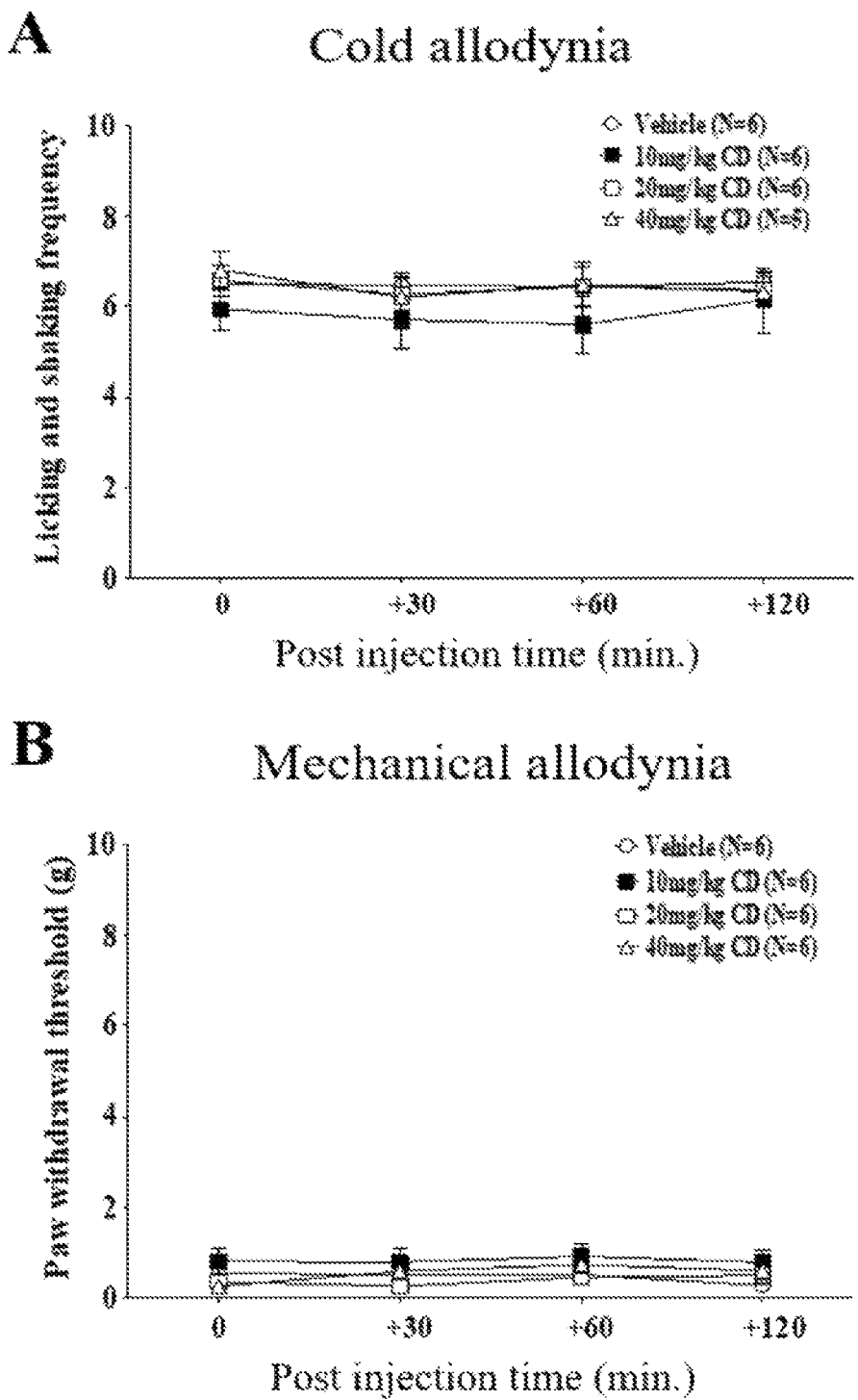
FIG. 6A-B

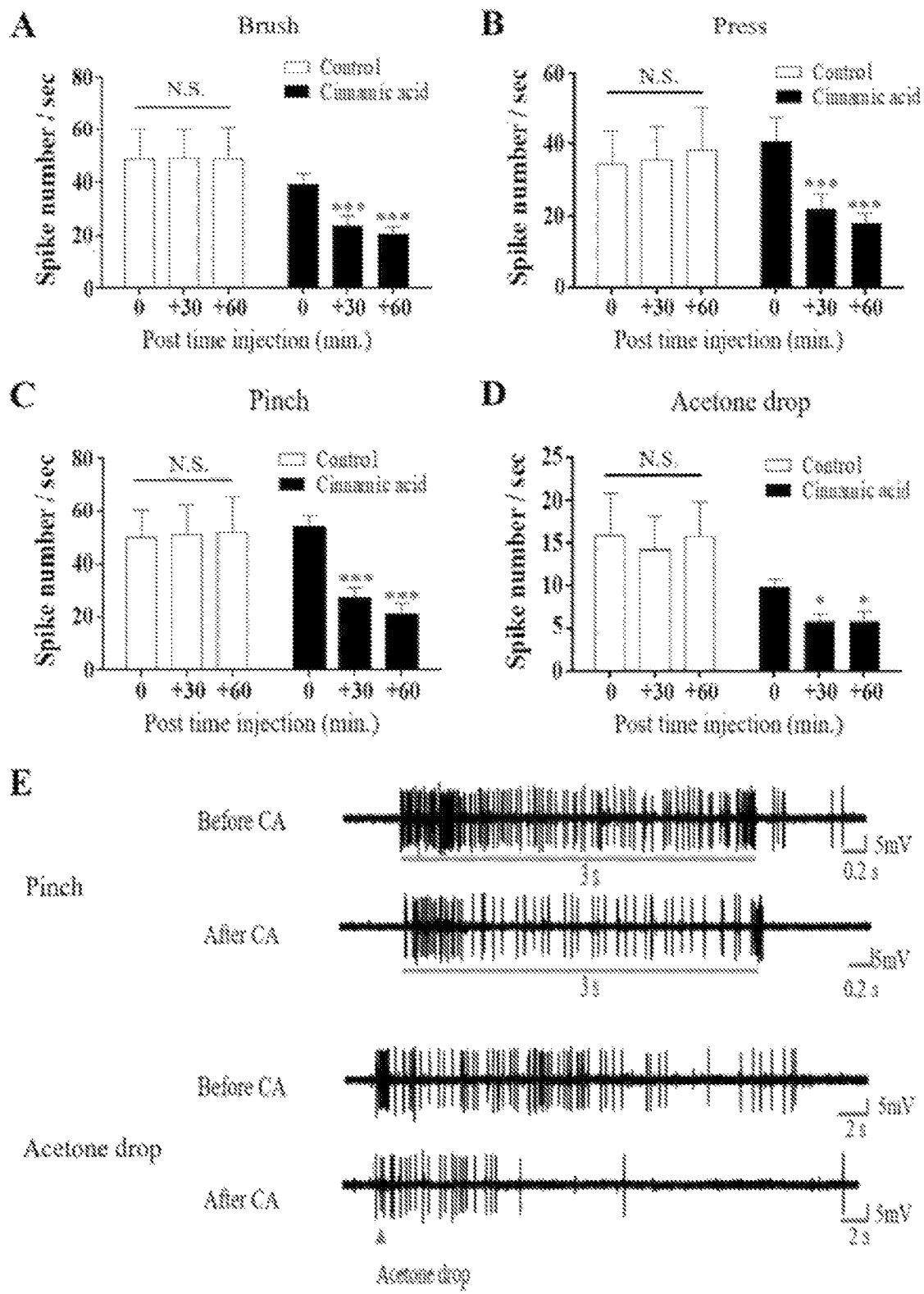
FIG. 7A-E

PHARMACEUTICAL COMPOSITION FOR PREVENTING OR TREATING ALLODYNIA CAUSED BY ANTICANCER AGENTS

CROSS REFERENCE TO RELATED APPLICATIONS

This application is a U.S. National Phase Application filed under 35 U.S.C. § 371 and claims priority to International Application No. PCT/KR2019/006887, filed Jun. 7, 2019, which application claims priority to Korean Patent Application No. 10-2018-0065562, filed Jun. 7, 2018, the disclosures of which are incorporated herein by reference.

TECHNICAL FIELD

The present disclosure relates to a pharmaceutical composition for preventing or treating allodynia caused by anticancer agents, containing cinnamic acid or a pharmaceutically acceptable salt thereof as an active ingredient.

BACKGROUND ART

Pain felt by humans may be largely divided into acute pain and chronic pain. According to the International Pain Research Institute, pain is defined as "an unpleasant sensory and emotional experience with actual or potential tissue damage", and if this pain symptom is classified by characteristics and duration, the pain may be divided into acute and chronic pain.

Acute pain, which results from nociceptive stimulation caused by tissue damage due to disease or trauma, includes childbirth pain, pain after surgery, pain after tissue damage, etc. and usually disappears within 3 to 6 months, and it is effectively treated by various drugs (narcotic pain relievers, nonsteroidal anti-inflammatory drugs).

Chronic pain is caused by nerve damage due to several unclear causes and subsequent changes in the nervous system, lasts longer than the healing period of the disease or damage caused, has unclear boundaries of the pain areas, shows persistent dull and deep pain, lasts more than 6 months, and is limited in terms of use of narcotic pain relievers or nonsteroidal anti-inflammatory drugs. For example, chronic pain includes migraine, rheumatic pain, diabetic pain, and cancer pain, and these pains drastically degrade patients' quality of life and may accompany depression and the like. Narcotic pain relievers have moderate effects, but side effects thereof are strong, making them difficult to use continuously, and nonsteroidal anti-inflammatory drugs are weak in effects (Joshi S K et al., Neuroscience. 2006 Dec. 1; 143(2):587-96; LaBuda C J et al., *J Neurosci Methods*. 2005 Jun. 15; 144(2):175-81). Currently, tricyclic antidepressant or anti-epileptic drug are used clinically, but the effects are known to be weak, and therefore, the development of a new drug is required.

Among chronic pain diseases, cancer pain may be divided into pain caused by the tumor itself, bone pain caused by carcinoma metastasized to the bone, and pain caused by treatment-related therapy, that is, anticancer agents.

Among the pains, that caused by anticancer agents is neuropathic pain, and this includes spontaneous pain, which occurs spontaneously without external stimulation, hyperalgesia, in which stimuli that usually cause pain are felt more painfully, and allodynia, where severe pain results even with mild stimuli that do not normally cause pain.

There are several types of allodynia, such as pain caused by mechanical stimulation (mechanical allodynia) and pain caused by cold stimulation (cold allodynia). Depending on the anticancer agents, the degree of mechanical allodynia and cold allodynia caused may be different.

Meanwhile, allodynia caused by anticancer agents is difficult to treat after occurrence, and even if the use of the drug is stopped, the pain lasts for several weeks to several months, sometimes lasting several years.

Accordingly, in the case of cancer treatment using anticancer agents, adequately suppressing allodynia has become a very important viewpoint in utilizing a strong anticancer effect of the drug.

For example, in Korean Patent No. 697212, there is disclosed a hematopoietic enhancer for treating side effects caused by administration of anticancer agents, containing a herbal mixture extract of Astragali Radix and Angelicae Gigantis Radix as an active ingredient. In Korean Patent No. 1133837, there is disclosed a composition for inhibiting kidney toxicity caused by administration of anticancer agents, containing an extract of Pulsatillae Radix as an active ingredient. In Korean Patent No. 1350143, there is disclosed a composition for reducing side effects caused by anticancer agents, containing extracts of Pinelliae Rhizoma and Scutellariae Radix as active ingredients. However, there is a problem in that most of these effects of inhibiting side effects interfere with the anticancer activity of the anticancer agents, thereby reducing the anticancer activity to a certain extent.

Meanwhile, cinnamic acid is a component of cinnamon, and cinnamic acid or its derivatives are known to have excellent physiological effects, such as anti-inflammatory, anticancer, antibacterial, and antiviral effects. Furthermore, it is known to be effective even in mental diseases acting on the central nervous system (CNS), such as ischemia, Parkinson's disease, Alzheimer's disease, and Huntington's disease. However, there is no known use for the prevention, improvement, or treatment of allodynia due to administration of anticancer agents.

DISCLOSURE

Technical Problem

The present inventors have made many efforts to develop a method capable of promoting safer cancer treatment by preventing or treating allodynia caused by anticancer agents, and as a result, they have found that cinnamic acid may prevent or treat allodynia caused by anticancer agents, thereby completing the present disclosure.

Technical Solution

An object of the present disclosure provides a pharmaceutical composition for preventing or treating allodynia caused by anticancer agents, containing cinnamic acid or a pharmaceutically acceptable salt thereof as an active ingredient.

Another object of the present disclosure provides a food composition for preventing or improving allodynia caused by anticancer agents, containing cinnamic acid or a food acceptable salt thereof as an active ingredient.

Yet another object of the present disclosure provides a pharmaceutical composition for preventing or treating allodynia caused by anticancer agents, containing an extract of *Cinnamomi cortex* as an active ingredient.

Still another object of the present disclosure provides a food composition for preventing or improving allodynia caused by anticancer agents, containing an extract of *Cinnamomi cortex* as an active ingredient.

Still yet another object of the present disclosure provides a method for preventing or treating allodynia caused by anticancer agents, including administering a composition containing cinnamic acid or a pharmaceutically acceptable salt thereof to a subject.

Still yet another object of the present disclosure provides a kit for preventing or treating cancer, including a first composition containing cinnamic acid or a pharmaceutically acceptable salt thereof; and a second composition containing an anticancer agent as an active ingredient.

Advantageous Effects

According to the present disclosure, the composition containing cinnamic acid or a pharmaceutically acceptable salt thereof is administered to a subject scheduled to receive anticancer agents or having received anticancer agents, thereby preventing, improving, or treating allodynia.

DESCRIPTION OF DRAWINGS

FIG. 4A-G is a diagram illustrating that a single injection of oxaliplatin induces neuropathic pain behavior and hyperexcitation of spinal neurons. Significant allodynia was induced in mice after 4 days after a single injection of oxaliplatin; (A) Cold allodynia; n=34. (B) Mechanical allodynia; n=31. (C to F) Excitation frequency of spinal WDR neurons to brush, press, pinch, and acetone drop stimulations after injection of 5% glucose (control, n=7) or oxaliplatin (n=7). (G) Typical raw traces of excitation of WDR neurons to pinch and acetone drop stimulations in a control and an oxaliplatin group. Data were represented as mean±S.E.M.; * $p<0.05$,  $p<0.01$, * $p<0.001$ vs. Before; by paired t-test (A, B) and * $p<0.05$,  $p<0.01$, * $p<0.001$ vs. Control; by unpaired t-test (C-F).

FIG. 5A-B is a diagram illustrating that intraperitoneal administration of cinnamic acid delays oxaliplatin-induced cold allodynia and mechanical allodynia. Cinnamic acid was injected intraperitoneally at three different concentrations (10 mg/kg, 20 mg/kg, and 40 mg/kg) on the 4th day (time point of 0 min) when oxaliplatin-treated mice showed significant signs of allodynia. Behavioral tests for (A) cold allodynia and (B) mechanical allodynia were performed before injection of cinnamic acid (time point 0 min) and at 30 min, 60 min, and 120 min after injection. A vehicle group was administered with 10% DMSO as a control. Data were represented as mean±S.E.M.; * $p<0.05$,  $p<0.01$, * $p<0.001$ vs. 0 min; by Bonferroni post-test after one-way ANOVA (A, B).

FIG. 6A-B is a diagram illustrating that intraperitoneal administration of cinnamaldehyde had no effect on the delay of oxaliplatin-induced cold allodynia and mechanical allodynia. Cinnamaldehyde was injected intraperitoneally at three different concentrations (10 mg/kg, 20 mg/kg, and 40 mg/kg) on the 4th day (time point 0 min) when oxaliplatin-treated mice showed significant signs of allodynia. Behavioral tests for (A) cold allodynia and (B) mechanical allodynia were performed before injection of cinnamaldehyde and after 30 min, 60 min, and 120 min after injection. A vehicle group was administered with 1% Tween 20 as a control. Data were represented as mean±S.E.M.; * $p<0.05$,  $p<0.01$, * $p<0.001$ vs. 0 min; by Bonferroni post-test after one-way ANOVA (A, B).

FIG. 7A-E is a diagram illustrating that cinnamic acid inhibits hyperexcitation of spinal WDR neurons in oxaliplatin-treated mice. Changes in excitation frequency of WDR neurons to cold allodynia and mechanical allodynia were measured through in vivo extracellular recording after intraperitoneal injection of cinnamic acid (20 mg/kg, i.p.) in oxaliplatin-treated mice (n=6). Changes in excitation frequency of WDR neurons to (A) brush, (B) press, (C) pinch, and (D) acetone drop stimulations. A control mouse (n=6) was administered with the same volume of 10% DMSO. Data were represented as mean±S.E.M.; * $p<0.05$, *** $p<0.001$ vs. time point 0 min; by Dunnett's multiple comparisons test after two-way ANOVA (A-D), N.S.; non-significant. (E) Typical raw traces of excitation of WDR neurons in response to pinch or acetone drop stimulation before and after injection of cinnamic acid.

BEST MODE FOR INVENTION

Figure 1:
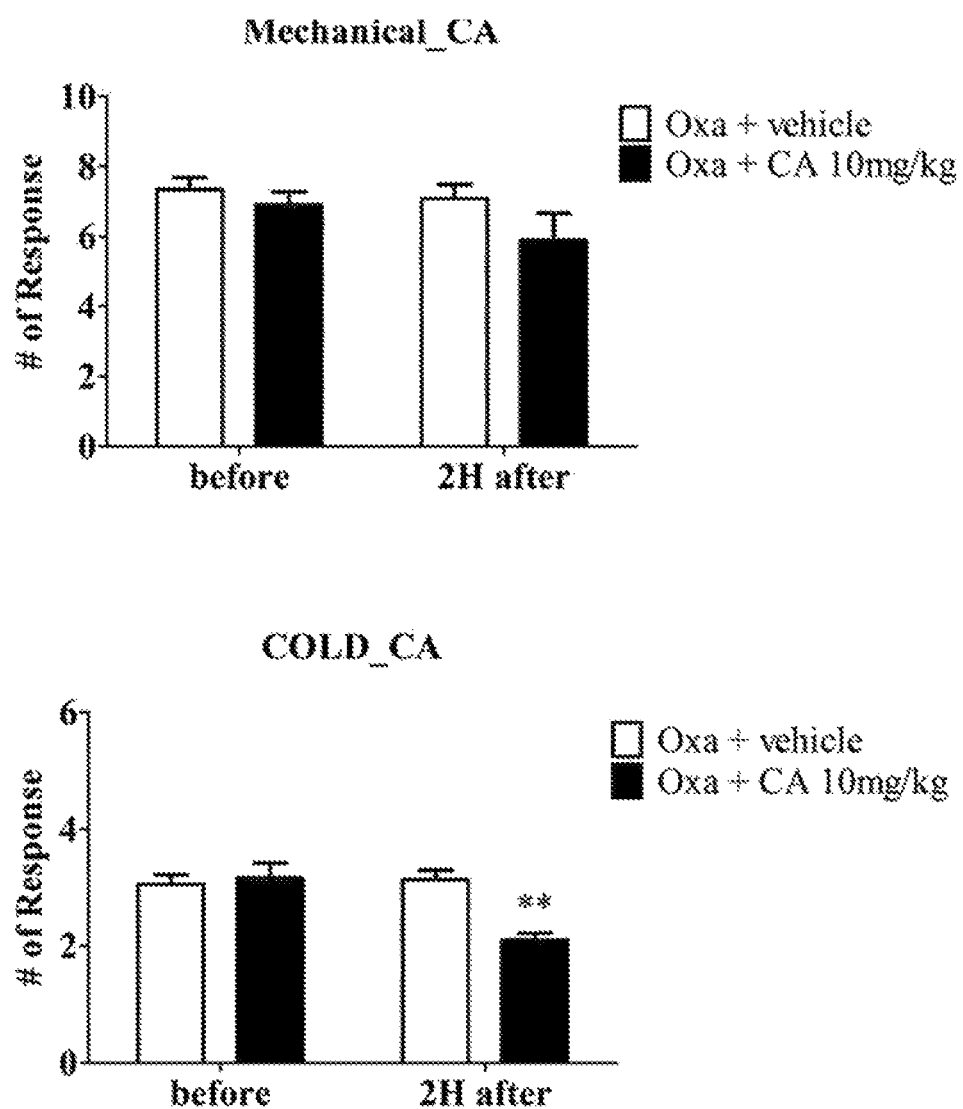
FIG. 1 is a diagram illustrating results of oral administration of cinnamic acid to an experimental animal group in which neuropathic pain is induced by an oxaliplatin anticancer agent.

The present disclosure will be specifically described as follows. Meanwhile, each description and embodiment disclosed in the present disclosure can also be applied to each other description and embodiment. That is, all combinations of various components disclosed in the present disclosure belong to the scope of the present disclosure. In addition, the specific description described below may not limit the scope of the present disclosure.

As an aspect of the present disclosure for solving the problems, the present disclosure provides a pharmaceutical composition for preventing or treating allodynia caused by anticancer agents, containing cinnamic acid or a pharmaceutically acceptable salt thereof as an active ingredient.

In the present disclosure, the 'cinnamic acid' is a compound represented by the following Chemical Formula 1, and is a component of cinnamon.

Chemical Formula 1

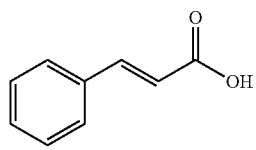

Cinnamon, which is a raw material of cinnamic acid, refers to the bark of *Cinnamomi cortex* of the Lauraceae or other closely related plants. Traditionally, in oriental medicine, there are known effects such as sanhanhaepyo (an effect of removing cold energy from the surface by sweating), ongyeongtongmaek (an effect of facilitating communication of stagnant meridians using hot drugs), and tongyanghwagi (an effect of passing energy and strengthening energy), etc. Many studies for such cinnamon have been conducted on action on the nerves, immunity and anticancer effects, and antibacterial effects, and have been traditionally used as prescriptions for Ongyeongtang, Gyejitang, Gyejiboknyeonghwan, Sogeonjungtang and Socheongnyongtang.

With the above-described characteristics, cinnamon is a widely used herbal medicine, and when the cinnamon is applied to the human body, side effects rarely occur; cinnamic acid, which is a component of cinnamon, may also be used without side effects.

The cinnamic acid may be purchased and used in a form which is already commercially available, and may be used in a form extracted and purified from herbal medicines such as cinnamon by methods known in the art, or it may be chemically synthesized.

In the present disclosure, the cinnamic acid represents the use of preventing or treating allodynia caused by anticancer agents. The cinnamic acid having the use includes any pharmaceutically acceptable forms, such as salts, isomers, esters, amides, thioesters, and solvates, but is not limited thereto.

The pharmaceutically acceptable salt of the cinnamic acid refers to a salt prepared according to a general method in the art, and such a preparation method is known to those skilled in the art. Specifically, the pharmaceutically acceptable salt includes pharmacologically or physiologically acceptable salts induced from the following inorganic acids and organic acids and bases, but is not limited thereto.

The acid addition salt is prepared by a general method, for example, by dissolving a compound in an excess acid aqueous solution and precipitating the salt using a water-miscible organic solvent, such as methanol, ethanol, acetone, or acetonitrile. The same molar amount of compound and acid or alcohol (e.g., glycol monomethyl ether) in water are heated, and then the mixture may be evaporated and dried, or the precipitated salt may be suction-filtered. Here, as the free acid, organic acids and inorganic acids may be used. As the inorganic acids, hydrochloric acid, phosphoric acid, sulfuric acid, nitric acid, tartaric acid, etc. may be used, and as the organic acids, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. may be used, but the free acid is not limited thereto.

The bases may also be used to prepare pharmaceutically acceptable metal salts. An alkali metal salt or an alkaline earth metal salt may be obtained, for example, by dissolving the compound in a large amount of an alkali metal hydroxide or alkaline earth metal hydroxide solution, filtering a non-dissolved compound salt, and then evaporating and drying a filtrate. In this case, the metal salt is pharmaceutically suitable for those prepared by, particularly, sodium, potassium, or calcium salts, but is not limited thereto. Further, silver salts corresponding thereto may be obtained by reacting the alkali metal or alkaline earth metal salt with a suitable silver salt (e.g., silver nitrate).

The term "anticancer agent" in the present disclosure refers to a prophylactic agent and a therapeutic agent for cancer. Examples of the anticancer agent include prophylactic and therapeutic agents for cancer causing peripheral nerve disorders as side effects, such as lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, gastric cancer (e.g., papillary adenocarcinoma, mucous adenocarcinoma, glandular squamous cell carcinoma), duodenal cancer, small intestine cancer, colon cancer (e.g., colon cancer, rectal cancer, anal cancer, familial colon cancer, hereditary nasal polyposis colon cancer, gastrointestinal interstitial tumor), breast cancer (e.g., invasive ductal cancer, non-invasive ductal cancer, inflammatory breast cancer), ovarian cancer (e.g., epithelial ovarian carcinoma, extra-testicular germ cell tumor, ovarian germ cell tumor, ovarian hypomalignant tumor), testicular tumor, prostate cancer (e.g., hormone-dependent prostate cancer, hormone-independent prostate cancer), liver cancer (e.g., hepatocellular carcinoma, primary liver cancer, extrahepatic bile duct cancer), thyroid cancer (e.g., medullary thyroid carcinoma), kidney cancer (e.g., renal cell carcinoma, transitional epithelial carcinoma of the renal pelvis and ureter), cervical cancer (e.g., cervical cancer, uterine body cancer, uterine sarcoma), brain tumors (e.g., medulloblastoma, glioma, pineal gonadoblastoma, spheroid gonadocytoma, diffuse gonadoblastoma, degenerative gonadoblastoma, pituitary adenoma), retinoblastoma, skin cancer (e.g., basal cell carcinoma, malignant melanoma), sarcoma (e.g., rhabdomyosarcoma, leiomyosarcoma, soft tissue sarcoma), malignant bone tumor, bladder cancer, blood cancer (e.g., multiple myeloma, leukemia, malignant lymphoma, Hodgkin's disease, chronic myelogenous disease), primary unknown cancer, etc.

Examples of these anticancer agents include taxane anticancer agents (e.g., paclitaxel (taxol), and doxetaxel), vinca alkaloid anticancer agents (e.g., vincristine, and vinblastine), platinum-based agents (e.g., cisplatin, carboplatin, and oxaliplatin), molecular targeted drugs (e.g., bortezomib), etc.

Among the anticancer agents described above, paclitaxel, vincristine, oxaliplatin, cisplatin, carboplatin and bortezomib are known as agents with allodynia, which is neuropathic pain as remarkable side effects (*J. Clin Oncol.* 24:1633-1642, 2006; *Neurotoxicology,* 27:992-1002, 2006; *British Journal of Haematology,* 127, 165-172, 2004).

The term "allodynia" used herein refers to a condition, a symptom, or a disease that causes severe pain even with weak stimulation that does not cause pain normally, and is a type of neuropathic pain. The allodynia includes several types of allodynia, such as pain caused by mechanical stimulation (mechanical allodynia) and pain caused by cold stimulation (cold allodynia).

Depending on an anticancer agent, the degrees of causing mechanical allodynia and cold allodynia may be different from each other (*J. Immunol.* 249:9-17, 2002). Oxaliplatin is known to specifically induce a high frequency of cold allodynia (*Toxicology* 234:176-184, 2007; *Cancer Chemother Pharmacol.* 25:299-303, 1990).

In an embodiment of the present disclosure, as a result of administering cinnamic acid to an animal model administered with an anticancer agent, it was confirmed that allodynia was relieved, and as a result, it was confirmed that the cinnamic acid may be effectively used for preventing or treating allodynia caused by anticancer agents.

Specifically, it was confirmed that when the cinnamic acid was administered orally, the cinnamic acid exhibited an excellent effect on cold allodynia, and it was confirmed that the relief of cold allodynia was strongly observed specifically in an oxaliplatin-administered group. In addition, when the cinnamic acid was injected intraperitoneally, the cinnamic acid had an excellent effect of alleviating cold allodynia and mechanical allodynia in the oxaliplatin-administered group. That is, the cinnamic acid of the present disclosure or a pharmaceutically acceptable salt thereof may be used in combination with a platinum-based anticancer agent causing cold allodynia or mechanical allodynia to exhibit a pain relief effect.

Meanwhile, the cinnamic acid not only minimizes side effects by relieving the allodynia, but may also maximize the anticancer activity by being administered in combination with an anticancer agent. That is, as compared with the case of single administration of an anticancer agent, the anticancer activity may be increased.

The pharmaceutical composition of the present disclosure has the use of "prevention" and/or "treatment" of allodynia caused by anticancer agents. For prophylactic use, the pharmaceutical composition of the present disclosure is administered to a subject who has the disease, disorder, or condition described herein or is suspected of being at risk of developing the disease. That is, the pharmaceutical composition of the present disclosure may be administered to a subject who is scheduled to receive anticancer agents or is at risk of developing allodynia due to the administration of anticancer agents. For therapeutic use, the pharmaceutical composition of the present disclosure is administered to a subject such as a patient already suffering from a disorder described herein in an amount sufficient to treat or at least partly stop the symptoms of the diseases, disorders, or conditions described herein. The amount effective for this use will vary according to the severity and course of the disease, disorder, or condition, previous treatment, the health condition of a subject and responsiveness to a drug, and the judgment of physicians or veterinarians.

Suitable carriers, excipients, or diluents which are commonly used in the preparation of the pharmaceutical composition of the present disclosure may be further included. At this time, the content of Compound 1 included in the composition is not particularly limited thereto, but may include 0.0001 wt % to 10 wt %, preferably 0.001 wt % to 1 wt % based on the total weight of the composition.

The pharmaceutical composition may have at least one formulation selected from the group consisting of tablets, pills, powders, granules, capsules, suspensions, oral liquids, emulsions, syrups, sterile aqueous solutions, non-aqueous solvents, suspensions, emulsions, lyophilized agents, and suppositories, and may be various oral or parenteral formulations. When the pharmaceutical composition is formulated, the formulation may be prepared by using diluents or excipients, such as a filler, an extender, a binder, a wetting agent, a disintegrating agent, and a surfactant, which are generally used. A solid formulation for oral administration includes a tablet, a pill, a powder, a granule, a capsule, and the like, and the solid formulation may be prepared by mixing at least one excipient, for example, starch, calcium carbonate, sucrose or lactose, gelatin, and the like with at least one compound. Further, lubricants such as magnesium stearate, talc, and the like may be used in addition to simple excipients. A liquid formulation for oral administration may correspond to a suspension, an oral liquid, an emulsion, a syrup, and the like, and may include various excipients, for example, a wetting agent, a sweetener, an aromatic agent, a preserving agent, and the like, in addition to water and liquid paraffin, which are commonly used as simple diluents. A formulation for parenteral administration includes sterilized aqueous solutions, non-aqueous solvents, suspensions, emulsions, lyophilized agents, and suppositories. As the non-aqueous solution and the suspension, propylene glycol, polyethylene glycol, vegetable oil such as olive oil, injectable ester such as ethyl oleate, and the like may be used. As a base of the suppository, witepsol, macrogol, tween 61, cacao butter, laurinum, glycerogelatin, and the like may be used.

The composition of the present disclosure may be administered to a subject in a pharmaceutically effective amount.

In the present disclosure, the term "pharmaceutically effective dose" refers to an amount sufficient to treat diseases at a reasonable benefit/risk ratio applicable to medical treatment, and an effective dose level may be determined according to factors including a kind of subject, the severity, age, gender, a type of disease, the activity of a drug, sensitivity to a drug, a time of administration, a route of administration, an excretion rate, duration of treatment, and agents to be simultaneously used, and other factors well known in the medical field. The composition of the present disclosure may be administered as an individual therapeutic agent or administered in combination with other therapeutic agents, and sequentially or simultaneously administered with conventional therapeutic agents. In addition, the composition of the present disclosure may be administered once or several times. It is important to administer an amount capable of obtaining a maximum effect with a minimal amount without side effects in consideration of all of the factors, and the amount thereof may be easily determined by those skilled in the art. A preferred dosage of the composition of the present disclosure varies depending on the condition and weight of a patient, the severity of a disease, the form of a drug, and the route and duration of administration, and the dosage may be administered once a day or administered several times. The composition is not particularly limited as long as it is a subject for the purpose of preventing or treating allodynia caused by anticancer agents, and any composition can be applied. The administration method is included without limitation as long as the method is a general method in the art. For example, the composition may be administered by oral, intraperitoneal, rectal or intravenous, intramuscular, subcutaneous, intrauterine dural, or intracerebrovascular injection.

The pharmaceutical composition of the present disclosure may be administered orally or injected intraperitoneally in an amount of 5 mg/kg to 100 mg/kg, and specifically, may be administered orally in an amount of 10 mg/kg to 100 mg/kg or injected intraperitoneally in an amount of 10 mg/kg to 40 mg/kg, but is not limited thereto. Specifically, according to an embodiment of the present disclosure, as a result of oral administration of cinnamic acid in an amount of 10 mg/kg to an experimental animal in which allodynia is induced by oxaliplatin, it was confirmed that cold allodynia caused by oxaliplatin was relieved. In addition, as a result of oral administration of cinnamic acid in an amount of 100 mg/kg to an experimental animal in which allodynia is induced by paclitaxel and vincristine, it was confirmed that cold allodynia caused by paclitaxel and vincristine was relieved. According to another embodiment of the present disclosure, as a result of intraperitoneal administration of cinnamic acid in an amount of 20 mg/kg to an experimental animal in which allodynia is induced by oxaliplatin, it was confirmed that mechanical allodynia and cold allodynia caused by oxaliplatin were relieved.

The pharmaceutical composition of the present disclosure may be administered to a subject who is scheduled to receive anticancer agents or to a subject who is receiving the anticancer agents to prevent the occurrence of allodynia or alleviate the degree of occurrence.

As another aspect of the present disclosure for solving the problems, the present disclosure provides a food composition for preventing or improving allodynia caused by anticancer agents, containing cinnamic acid or a food acceptable salt thereof as an active ingredient.

The terms used herein are the same as those described above.

In the present disclosure, the term "improvement" refers to all actions which improve or benefit symptoms of a subject who is suspected of and has developed allodynia caused by anticancer agents by using the composition containing cinnamic acid or a food acceptable salt thereof as an active ingredient.

As the food acceptable salt of the present disclosure, an acid addition salt formed by a food acceptable free acid or a metal salt formed by a base is useful. As an example, inorganic acids and organic acids may be used as the free acid. As the inorganic acids, hydrochloric acid, sulfuric acid, bromic acid, sulfurous acid, or phosphoric acid may be used, and as the organic acids, citric acid, acetic acid, maleic acid, fumaric acid, gluconic acid, methanesulfonic acid, and the like may be used. In addition, as the metal salt, an alkali metal salt or alkaline earth metal salt such as a sodium, potassium, or calcium salt may be used. However, the present disclosure is not necessarily limited thereto.

The food composition for preventing or improving allodynia caused by the anticancer agents of the present disclosure includes forms of pills, powders, granules, infusions, tablets, capsules or liquids, and the food added with the composition of the present disclosure includes various foods, for example, beverages, gums, teas, vitamin complexes, health supplements, etc.

As an essential ingredient that may be included in the food composition of the present disclosure, other ingredients other than those containing the compound represented by Chemical Formula 1 above are not particularly limited, and various herbal extracts, food supplements, or natural carbohydrates may be contained as additional ingredients like general foods. In the food composition, the mixed amount of the essential ingredient may be suitably determined according to the purpose of use (prevention, improvement, healthy or therapeutic treatment).

In addition, the food supplements include general food additives in the art, for example, flavoring agents, tasting agents, coloring agents, fillers, stabilizers, and the like.

Examples of the natural carbohydrates may include general sugars, such as monosaccharides, for example, glucose, fructose, and the like; disaccharides, for example, maltose, sucrose, and the like; and polysaccharides, for example, dextrin, cyclodextrin, and the like, and sugar alcohols such as xylitol, sorbitol, erythritol, and the like. In addition to those described above, as the flavoring agent, natural flavoring agents (e.g., rebaudioside A, glycyrrhizin, etc.) and synthetic flavoring agents (saccharin, aspartame, etc.) may be advantageously used.

In addition, the food composition of the present disclosure may contain various nutrients, vitamins, minerals (electrolytes), flavoring agents such as synthetic and natural flavoring agents, coloring agents, and enhancers (cheese, chocolate, etc.), pectic acid and salts thereof, alginic acid and salts thereof, an organic acid, a protective colloidal thickener, a pH adjusting agent, a stabilizer, a preservative, glycerin, alcohol, a carbonic acid agent used in a carbonated drink, and the like. In addition, the food composition of the present disclosure may contain flesh for preparing natural fruit juice and fruit juice beverages and vegetable beverages. These ingredients may be used independently or in combination.

In the present disclosure, the health supplement food includes health functional foods and health foods. The health functional food is the same term as food for special health use (FoSHU), and refers to food with a high medical/care effect, which is processed so that a bioregulatory function is effectively shown in addition to nutrition supply. Here, "functionality" refers to regulating nutrients to the structure and function of the human body or obtaining effects useful for health applications such as physiological action. The food of the present disclosure may be prepared by methods which are commonly used in the art and may be prepared by adding raw materials and ingredients which are commonly added in the art in preparation. In addition, the formulation of the food may be prepared without limitation as long as the formulation is recognized as food. The food composition of the present disclosure may be prepared in various forms of formulations, and unlike general drugs, the food composition has an advantage of having no side effects that may occur when taking a drug for a long period of time using food as a raw material, and is excellent in portability.

The allodynia may be cold allodynia or mechanical allodynia, but is not limited thereto.

As yet another aspect of the present disclosure for solving the problems, the present disclosure provides a pharmaceutical composition for preventing or treating allodynia caused by anticancer agents, containing an extract of *Cinnamomi cortex* as an active ingredient.

The terms used herein are the same as those described above.

The term "*Cinnamomi Cortex*" in the present disclosure is the stem bark of *Cinnamomum cassia* Presl, a Lauraceae plant, which is used as it is or slightly removed with the periderm, and has a unique odor and tastes slightly sweet and spicy. The *Cinnamomi cortex* may vary in quality depending on a region, and is produced in Vietnam, China, Indonesia, Taiwan, Turkey, Thailand, etc. In the present disclosure, the term "*Cinnamomi Cortex*" may be used interchangeably with the term "cinnamon".

The extraction method used when preparing the extract may preferably use, but is not limited thereto, methods, such as boiling water extraction, hot water extraction, cold needle extraction, reflux cooling extraction, or ultrasonic extraction.

The extract may be prepared by extraction with the extraction solvent or by adding a fractionation solvent to the extract prepared by extraction with the extraction solvent and fractionating. The extraction solvent is not limited thereto, but may use water, an organic solvent, or a mixed solvent thereof, and the organic solvent may use a polar solvent such as alcohol having 1 to 4 carbon atoms, ethyl acetate or acetone, a non-polar solvent such as hexane or dichloromethane, or a mixed solvent thereof. In addition, the extract may be more preferably a hot water extract, but is not limited thereto. The extract may be contained in an amount of 0.001 wt % to 100 wt %, more preferably 0.1 wt % to 80 wt %, based on the total weight of the pharmaceutical composition.

The pharmaceutical composition may contain cinnamic acid or a pharmaceutically acceptable salt thereof.

The term "cinnamic acid" and the pharmaceutically acceptable salt are the same as those described above.

In an embodiment of the present disclosure, as a result of administering a hot water extract of *Cinnamomi cortex* to an animal model administered with an anticancer agent, it was confirmed that allodynia was relieved, and as a result, it was confirmed that the hot water extract of *Cinnamomi cortex* may be effectively used for preventing or treating allodynia caused by anticancer agents.

Specifically, it was confirmed that when the hot water extract of *Cinnamomi cortex* was administered orally, the hot water extract of *Cinnamomi cortex* exhibited an excellent effect of alleviating cold allodynia and mechanical allodynia in a paclitaxel-administered group. That is, the extract of *Cinnamomi cortex* of the present disclosure may be used in combination with a taxane-based anticancer agent causing cold allodynia or mechanical allodynia to exhibit a pain relief effect.

Meanwhile, the extract of *Cinnamomi cortex* not only minimizes side effects by relieving the allodynia, but may also maximize the anticancer activity by being administered in combination with an anticancer agent. That is, as compared with the case of single administration of an anticancer agent, the anticancer activity may be increased.

The effect of the extract of *Cinnamomi cortex* may be an effect exerted by cinnamic acid or a pharmaceutically acceptable salt thereof contained in the hot water extract of *Cinnamomi Cortex*. Specifically, when the hot water extract of *Cinnamomi cortex* is administered orally, in the hot water extract of *Cinnamomi cortex* from Vietnam with a high cinnamic acid content, it was shown that an effect of relieving cold allodynia and mechanical allodynia is excellent as compared with a hot water extract of *Cinnamomi cortex* from China or Indonesia with a lower cinnamic acid content than that of *Cinnamomi cortex* from Vietnam, but it was suggested that the cinnamic acid plays an important role in the reduction of allodynia induced by anticancer agents. That is, the cinnamic acid of the present disclosure or a pharmaceutically acceptable salt thereof, and the extract of *Cinnamomi cortex* containing the same may be used in combination with a taxane-based anticancer agent causing cold allodynia or mechanical allodynia to exhibit a pain relief effect.

The pharmaceutical composition may be orally administered in an amount of 50 mg/kg to 500 mg/kg, and specifically, may be orally administered in an amount of 200 mg/kg to 500 mg/kg. According to an embodiment of the present disclosure, as a result of oral administration of a hot water extract of *Cinnamomi cortex* in an amount of 200 mg/kg to an experimental animal in which allodynia is induced by paclitaxel, it was confirmed that cold allodynia and mechanical allodynia caused by paclitaxel were alleviated.

The pharmaceutical composition may be administered to a subject who is scheduled to receive anticancer agents or to a subject who is receiving the anticancer agents to prevent the occurrence of allodynia or alleviate the degree of occurrence.

As yet another aspect of the present disclosure for solving the problems, the present disclosure provides a food composition for preventing or improving allodynia caused by anticancer agents, containing an extract of *Cinnamomi cortex* as an active ingredient.

The terms used herein are the same as those described above.

There is no particular limitation on other ingredients except for containing the hot water extract of *Cinnamomi cortex* as an essential ingredient that may be included in the food composition.

The extract of *Cinnamomi cortex* may contain cinnamic acid or a food acceptable salt thereof.

The extract of *Cinnamomi cortex* may be a hot water extract of *Cinnamomi Cortex*, but is not limited thereto.

The allodynia may be cold allodynia or mechanical allodynia, but is not limited thereto.

As yet still another aspect of the present disclosure for solving the problems, the present disclosure provides a method for preventing or treating allodynia caused by anticancer agents, including administering a composition containing cinnamic acid or a pharmaceutically acceptable salt thereof to a subject.

The terms used herein are the same as those described above.

In the present disclosure, the term "subject" refers to all animals including humans who are scheduled to receive anticancer agents or who have developed or may develop allodynia by administering anticancer agents, and the pharmaceutical composition of the present disclosure may be administered to a subject suspected of allodynia caused by anticancer agents to efficiently treat the subject.

The term "administration" in the present disclosure means introducing the pharmaceutical composition of the present disclosure to a subject suspected of allodynia caused by anticancer agents by any suitable method, and the pharmaceutical composition of the present disclosure may be administered through various oral or parenteral routes which may reach a target tissue.

The pharmaceutical composition of the present disclosure may be administered in a pharmaceutically effective dose.

In the present disclosure, the term "pharmaceutically effective dose" refers to an amount sufficient to treat diseases at a reasonable benefit/risk ratio applicable to medical treatment, and an effective dose level may be determined according to factors including a kind of subject, the severity, age, gender, a type of disease, the activity of a drug, sensitivity to a drug, a time of administration, a route of administration, an excretion rate, duration of treatment, and agents to be simultaneously used, and other factors well known in the medical field. The composition of the present disclosure may be administered as an individual therapeutic agent or administered in combination with other therapeutic agents, and sequentially or simultaneously administered with conventional therapeutic agents. In addition, the pharmaceutical composition may be administered once or several times. It is important to administer an amount capable of obtaining a maximum effect with a minimal amount without side effects in consideration of all of the factors, and the amount thereof may be easily determined by those skilled in the art.

The pharmaceutical composition of the present disclosure is not particularly limited as long as it is a subject for the purpose of preventing or treating allodynia caused by anticancer agents, and any composition can be applied. For example, in addition to humans, non-human animals such as monkeys, dogs, cats, rabbits, marmots, rats, mice, cows, sheep, pigs, goats, birds, fish, etc. may be used, and the pharmaceutical composition may be administered parenterally, subcutaneously, intraperitoneally, intrapulmonally, and intranasally, and for local treatment, if necessary, the pharmaceutical composition may be administered by any suitable method including intralesional administration. A preferable dose of the pharmaceutical composition of the present disclosure varies according to the condition and weight of a patient, the degree of a disease, a type of drug, and the route and period of administration, but may be properly selected by those skilled in the art. For example, the pharmaceutical composition may be administered by oral, intraperitoneal, rectal or intravenous, intramuscular, subcutaneous, intrauterine dural, or intracerebrovascular injection, but is not limited thereto.

A suitable total daily use amount may be determined by a physician within a range of correct medical judgment, and generally, an amount of 0.001 mg/kg to 1000 mg/kg, specifically an amount of 0.05 mg/kg to 1000 mg/kg, more specifically an amount of 5 mg/kg to 500 mg/kg may be administered once to several times a day.

The composition containing the cinnamic acid or the pharmaceutically acceptable salt thereof may be an extract of *Cinnamomi Cortex*, but is not limited thereto.

The extract of *Cinnamomi cortex* may be a hot water extract of *Cinnamomi Cortex*, but is not limited thereto.

As still yet another aspect of the present disclosure for solving the problems, the present disclosure provides a kit for preventing or treating cancer, including a first composition containing cinnamic acid or a pharmaceutically acceptable salt thereof; and a second composition containing an anticancer agent as an active ingredient.

The terms used herein are the same as those described above.

The first composition may include an extract of *Cinnamomi cortex* containing cinnamic acid or a pharmaceutically acceptable salt thereof, but is not limited thereto.

The extract of *Cinnamomi cortex* may be a hot water extract of *Cinnamomi Cortex*, but is not limited thereto.

The kit of the present disclosure refers to a tool that can be used for preventing or treating cancer, including each of the first composition and the second composition. The type of kit is not particularly limited, and a kit commonly used in the art may be used.

The kit of the present disclosure may be packaged in a form in which the first composition and the second composition are each contained in individual containers, or contained in one container divided into one or more compartments, and the first composition and the second composition each may be packaged in a unit dosage form of a single dose.

The first composition and the second composition in the kit may be separately administered in combination at an appropriate time according to a health condition of a subject to be administered.

That is, the route and frequency of administration of the first composition and the second composition may each be independent.

The kit of the present disclosure may further include an instruction manual describing a dosage, an administration method, and a frequency of administration for each of the first composition and the second composition.

According to still yet another aspect of the present disclosure, there is provided a method of preventing or treating cancer using the kit.

MODE FOR INVENTION

Hereinafter, configurations and effects of the present disclosure will be described in more detail through Examples. The following Examples are only provided for illustrating the present disclosure, and the scope of the present disclosure is not limited by the following Examples.

Example 1—Preparation of Composition for Intraperitoneal Administration Containing Cinnamic Acid Cinnamic acid (Wako) was dissolved in a Tween 80 solvent to prepare a composition having a concentration of 2 mg/mL.

Experimental Example 1—Test for Pain Relief when Cinnamic Acid was Administered in Anticancer Agent Pain Model Preparation of Animal Model Six-week-old mice (c57/bl6 mice) were prepared as an experimental animal.

(1) Oxaliplatin Animal Model

Oxaliplatin (Sigma-Aldrich) dissolved in a 5% glucose solution at a concentration of 2 mg/mL was singly administered intraperitoneally to the experimental animal in an amount of 6 mg/kg. Significant pain was observed from about 3 days after intraperitoneal administration.

(2) Paclitaxel Animal Model

Paclitaxel (Sigma-Aldrich) dissolved at a concentration of 6 mg/mL in a 1:1 solution of Cremophor EL and ethanol was diluted to a concentration of 2 mg/mL and intraperitoneally injected 4 times at 2 mg/kg. The dosage was administered every other day on days 0, 2, 4, and 6. Significant pain was observed from about 10 days after the first dosage.

(3) Vincristine Animal Model

Vincristine at a concentration of 1 mg/mL was injected intraperitoneally for 7 consecutive days at 0.1 mg/kg. Significant pain was observed from about 10 days after the first injection.

Evaluation Method for Cold Allodynia and Mechanical Allodynia (1) Evaluation Method for Cold Allodynia The reaction that occurred by applying about 20 μL of acetone to the soles of both rear paws of the experimental animal was observed and recorded for about 15 s.

Behaviors that are criteria for recording are an avoidance reaction, a behavior of shaking the soles of the paw, and a behavior of licking the soles of the paw. The evaluation was repeated a total of three times, and the average of the number of recorded behaviors was confirmed.

(2) Evaluation Method for Mechanical Allodynia

The number of reactions was recorded by stimulating the soles of both hind paws of the experimental animal 10 times using a von Frey filament at a pressure of 0.4 g.

The behaviors that are criteria for recording are an avoidance reaction and a behavior of licking the soles of the paw. The recording for both paws was averaged and confirmed.

Experiment Schedule (1) Oxaliplatin Administered Group

Experimental animals induced with allodynia were selected through a pre-behavioral experiment, and the effects were confirmed at 2 h after oral administration of 10 mg/kg of cinnamic acid.

(2) Paclitaxel Administered Group

As a pre-behavioral experiment, 50 mg/kg and 100 mg/kg of cinnamic acid was orally administered to experimental animals induced with allodynia, and the effects after 1 h and 2 h were confirmed.

(3) Vincristine Administered Group

Experimental animals induced with allodynia were selected through a pre-behavioral experiment and orally administered with 50 mg/kg and 100 mg/kg of cinnamic acid, and the effects after 1 h and 2 h were confirmed.

Experiment Results (1) Oxaliplatin-Administered Group

FIG. 1 illustrates results of oral administration of cinnamic acid to an experimental animal group in which neuropathic pain was induced by an oxaliplatin anticancer agent. For mechanical allodynia, no significant pain relief effect was observed compared to a control (vehicle), but for cold allodynia, a significant pain relief effect was observed at 2 h of administration compared to the control.

(2) Paclitaxel-Administered Group

Figure 2:
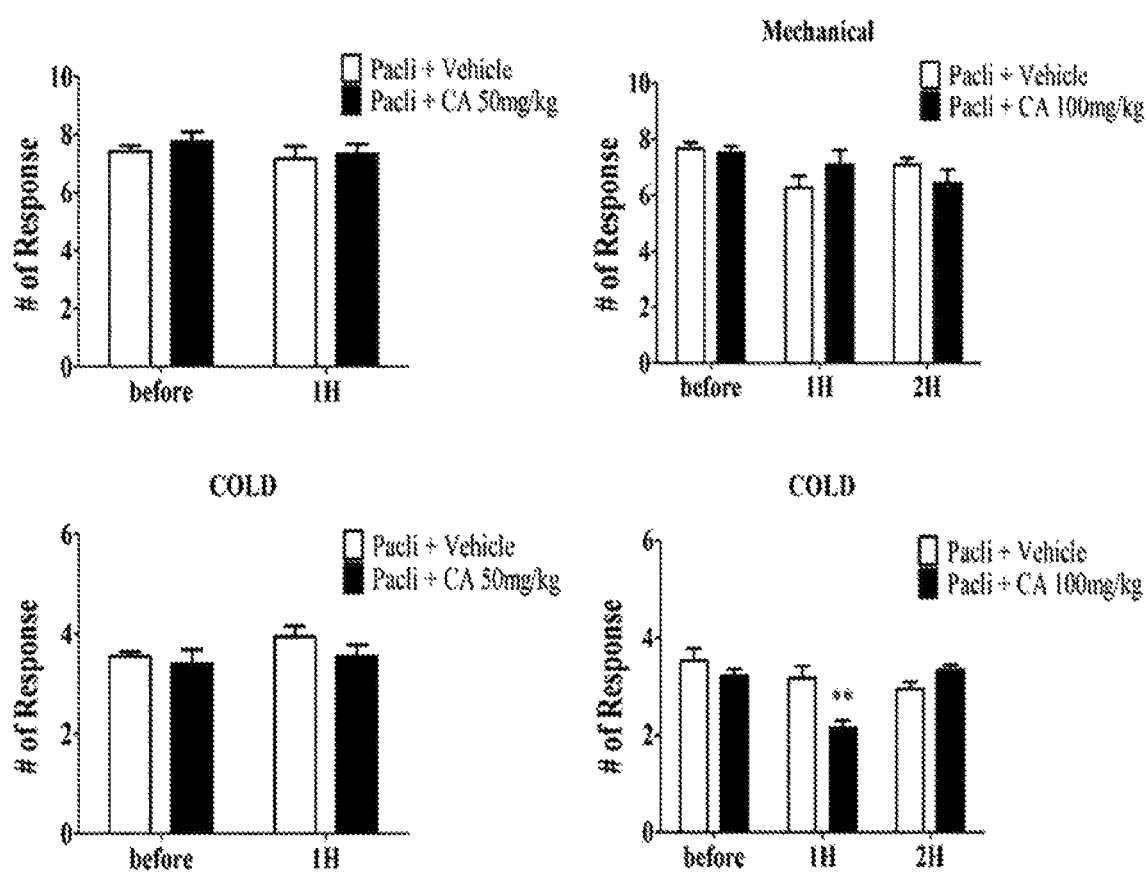
FIG. 2 is a diagram illustrating results of oral administration of cinnamic acid to an experimental animal group in which neuropathic pain is induced by a paclitaxel anticancer agent.

FIG. 2 illustrates results of oral administration of cinnamic acid to an experimental animal group in which neuropathic pain was induced by a paclitaxel anticancer agent. As a result of oral administration of 50 mg/kg of cinnamic acid, no significant pain relief effect was observed in both mechanical allodynia and cold allodynia. As a result of oral administration of 100 mg/kg of cinnamic acid, for mechanical allodynia, no significant pain relief effect was observed compared to the control, but for cold allodynia, a significant pain relief effect was shown after 1 h compared to the control.

(3) Vincristine Administered Group

Figure 3:
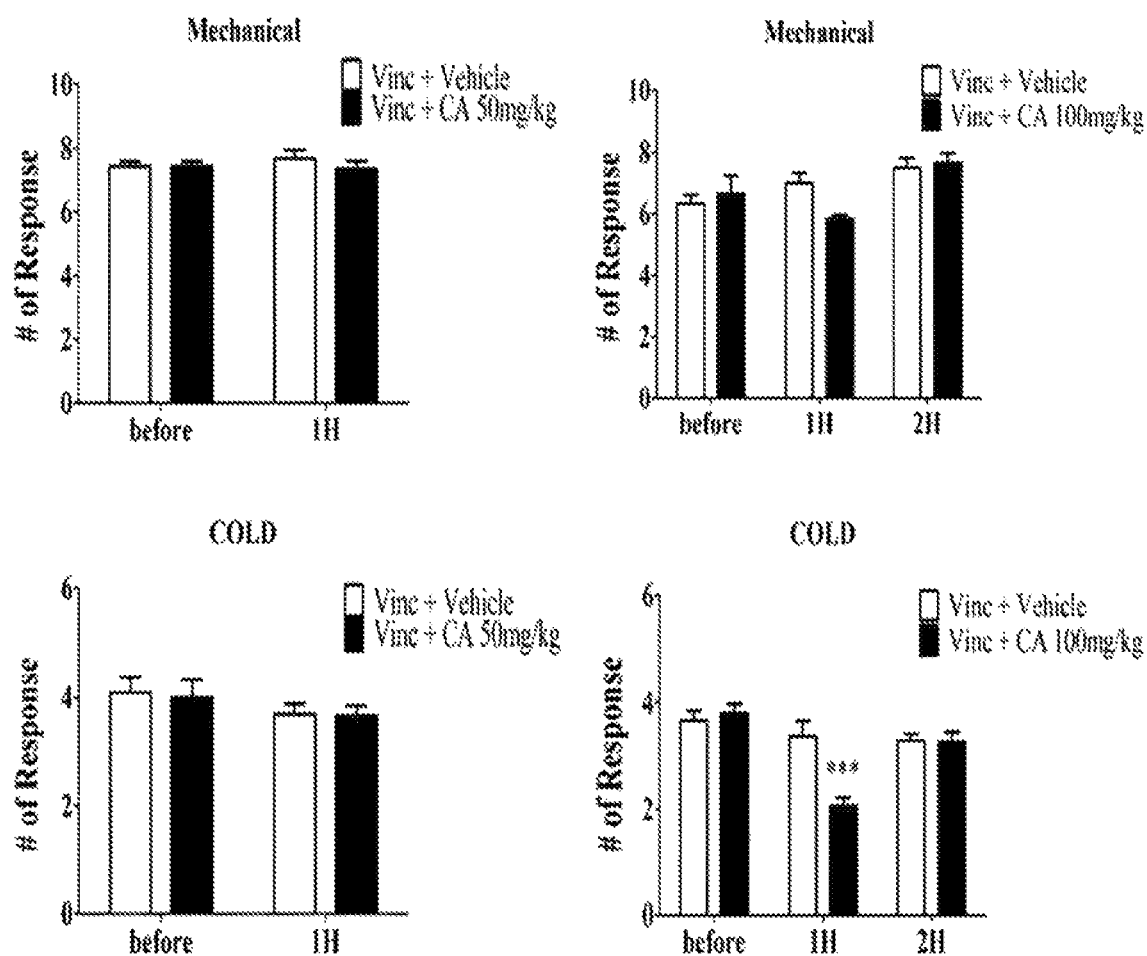
FIG. 3 is a diagram illustrating results of oral administration of cinnamic acid to an experimental animal group in which neuropathic pain is induced by a vincristine anticancer agent.

FIG. 3 illustrates results of oral administration of cinnamic acid to an experimental animal group in which neuropathic pain was induced by a vincristine anticancer agent. As a result of oral administration of 50 mg/kg of cinnamic acid, no significant pain relief effect was observed in both mechanical allodynia and cold allodynia. As a result of oral administration of 100 mg/kg of cinnamic acid, for mechanical allodynia, no significant pain relief effect was observed compared to the control, but for cold allodynia, a significant pain relief effect was shown after 1 h compared to the control.

Thus, as a result of oral administration of cinnamic acid to the animal experimental group in which pain was induced by three anticancer agents, it can be seen that mechanical allodynia is not significantly inhibited, whereas a significant pain relief effect is shown specifically only for cold allodynia.

In particular, for cold allodynia induced by oxaliplatin, the pain relief effect was shown up to 2 h after administration of a low dose (10 mg/kg, p.o.), whereas for cold allodynia induced by other anticancer agents (paclitaxel and vincristine), the pain relief effect was shown up to 1 h after administration of a high dose (100 mg/kg, p.o.). In other words, it can be seen that the pain relief effect on cold allodynia was particularly strongly shown in the oxaliplatin anticancer agent model, and weakly shown in the cold allodynia model caused by other anticancer agents (paclitaxel and vincristine).

Example 2—Preparation of Composition for Intraperitoneal Administration Containing Cinnamic Acid or Cinnamaldehyde Cinnamic acid (trans-cinnamic acid, Wako Pure Chemical Industries, Osaka, Japan) and cinnamaldehyde (Wako Pure Chemical Industries, Osaka, Japan) were dissolved in 10% dimethyl sulfoxide (DMSO, Sigma) (adjusted to pH 7 with 2 M HCl and 5 M NaOH) and 1% Tween 20 (Sigma), respectively. The final volume of 10% DMSO and 1% Tween 20 used in the experiment was 2 L/g rat. Cinnamic acid and cinnamaldehyde (10 mg/kg, 20 mg/kg, and 40 mg/kg) (i.p.) at different concentrations were administered to rats with cold allodynia and mechanical allodynia.

Experimental Example 2—Test for Pain Relief when Cinnamic Acid was Administered in Neuropathic Pain Model Experimental Animals Seven-week-old male Sprague Dawley (SD) rats (180 g to 210 g, 95 rats total, Young Bio, Gyeonggi, Korea) were fed freely with feed and water in cages. The room temperature was maintained at 23±2° C. and a 12 h/12 h contrast cycle was maintained. All procedures described in the present disclosure were approved by the Animal Care and Use Committee of Kyunghee University (KHUASP[SE]-18-153) and followed the guidelines of the International Pain Research Association.

Behavioral Experiment and Experimental Protocol

In order to measure cold allodynia and mechanical allodynia, according to a previous method (Flatters, S J; Bennett, G J Ethosuximide reverses paclitaxel- and vincristine-induced painful peripheral neuropathy. Pain 2004, 109, 150-161), an acetone drop test and a von Frey filament test (up-down method, Linton Instrumentation, Norfolk, UK) were performed, respectively. The rats were trained for one week before the start of the experiment to adapt to the touch and the experimental procedure. The rats were stabilized for 30 min before testing in a clear plastic box (20 cm×20 cm×14 cm) with a wire mesh bottom, while not recognizing the injection of oxaliplatin and other drugs.

For the cold allodynia test, acetone (10 μL) was dripped to the abdominal surface of the right hind paw through a pipette connected to a rubber tube, and the behavioral reaction was observed for 20 s. Acetone was dripped 5 times on the right hind paw, and the total frequency of licking and shaking of the soles was measured as an average per time.

For the mechanical allodynia test, paw withdrawal thresholds were measured in the right hind paw using a von Frey filament. Dixon's up-down method and Chaplan's calculation method were used, and a withdrawal threshold of 15 g was measured as a cut-off. In order to confirm the effects of cinnamaldehyde and cinnamic acid at different concentrations over time, the behavioral experiment was performed before injection of cinnamic acid and cinnamaldehyde (time point of 0 min) and at time points of 30 min, 60 min, and 120 min after injection.

Oxaliplatin Administration

Oxaliplatin (Wako Pure Chemical Industries, Osaka, Japan) was dissolved in a 5% glucose solution at a concentration of 2 mg/mL and injected intraperitoneally at a dose of 6 mg/kg. The same volume of 5% glucose solution (i.p.) was administered to a control.

In Vivo Extracellular Recording

Extracellular recording was performed on the 4th day after the administration of oxaliplatin for rats exhibiting cold allodynia and mechanical allodynia. The rats were anesthetized with urethane (Sigma; 1.5 g/kg, i.p.), and the spinals fixed to a stereotaxic frame were exposed to T13-L2 flowing at 10 mL/min to 15 mL/min at 38±1° C. and oxygenated (95% $O_2$/5% $CO_2$ gas) Krebs solution (in mM: 117 NaCl, 3.6 KCl, 2.5 $CaCl_2$, 1.2 $MgCl_2$, 1.2 $NaH_2PO_4$, 11 glucose, 25 $NaHCO_3$). Wide Dynamic Range (WDR) neurons were identified based on the response to brush, pressure, pinch, and acetone stimulations. Extracellular single-unit recording was made using a low-impedance insulated tungsten microelectrode (impedance 10 MW, FHC, Bowdoin, Me., USA). Mechanical stimulation was applied on the outside of the hind paw and the abdominal surface with brush, press, and pinch stimulations. The brush stimulation was applied by brushing a receiving site 5 times with a camel brush. The press stimulation was applied by pressing the receiving site for 4 s using a blunt tip of a camel hair brush having a diameter of about 0.5 g and a size of about 20 g. The pinch stimulation was applied by pinching the skin for 3 s using tooth forceps (11022-14, Fine Science Tool, Heidelberg, Germany). For cold stimulation, an acetone drop of 10 μL was applied to the receiving site.

Statistics

All data are expressed as mean±S.E.M. (Standard error of the mean). The data in FIG. 4 was analyzed by a paired t-test (FIGS. 4A and 4B) or an unpaired t-test (FIG. 4C). The data in FIGS. 5 and 6 were expressed as mean±S.E.M. and analyzed by a Bonferroni post-test after one-way ANOVA to evaluate a statistical difference between groups. The data in FIG. 7A were analyzed using Dunnett's multiple comparisons test after two-way ANOVA. The 95% reliability was considered to be statistically significant.

Experiment Results (1) Behavioral and Electrophysiological Association Test of Oxaliplatin-Induced Neuropathic Pain in Rats Intraperitoneal injection of oxaliplatin (6 mg/kg) caused neuropathic pain in rats. Significant cold allodynia and mechanical allodynia were observed from 3 to 7 days after the injection of oxaliplatin. FIGS. 4A and 4B are results of acetone drop and von Frey stimulation results before and after oxaliplatin injection. On day 4 after oxaliplatin injection, both cold allodynia and mechanical allodynia were significantly induced ($p<0.001$). After the behavioral signs of neuropathic pain were observed, in vivo extracellular recording was performed on the spinal neurons of rats. The number of spike responses to mechanical (brush, press, and pinch) and cold (acetone drop) stimulations of WDR neurons significantly increased after oxaliplatin injection to exhibit hyperexcitation of WDR neurons due to skin stimulation (FIGS. 4C to 4F). Typical raw traces of the responses of WDR neurons to pinch and acetone drop were shown in FIG. 4G. From these behavioral and electrophysiological results, it was confirmed that neuropathic pain appeared after 4 days of the injection of oxaliplatin.

(2) Relief Effect Test of Oxaliplatin-Induced Cold Allodynia and Mechanical Allodynia Due to Cinnamic Acid As a result of a behavioral test using three different doses (10 mg/kg, 20 mg/kg, and 40 mg/kg, i.p.) of cinnamic acid to determine whether cinnamic acid may reduce cold allodynia and mechanical allodynia caused by oxaliplatin, all three doses of cinnamic acid had effects on cold allodynia. The effect of 10 mg/kg of cinnamic acid was shorter than that of 20 mg/kg and 40 mg/kg of cinnamic acid as the effect disappeared at a time point of 120 min. At 20 mg/kg and 40 mg/kg, the pain relief effect of 20 mg/kg of cinnamic acid was slightly stronger than that of 40 mg/kg of cinnamic acid (control vs. 20 mg/kg, $p<0.001$ and 40 mg/kg, $p<0.05$) (FIG. 5A). In mechanical allodynia, 10 mg/kg of cinnamic acid showed a remarkable effect at 60 min after injection, so there was a slight effect, but 20 mg/kg of cinnamic acid had the strongest anti-allodynic effect among the three doses at all time points (FIG. 5B). These results indicated that intraperitoneal administration of cinnamic acid significantly alleviated cold allodynia and mechanical allodynia caused by oxaliplatin in rats, and the optimal dose thereof was 20 mg/kg.

(3) Relief Effect Test of Oxaliplatin-Induced Cold Allodynia and Mechanical Allodynia Due to Cinnamaldehyde As a result of the same experiment as cinnamic acid for oxaliplatin-induced cold allodynia and mechanical allodynia for cinnamaldehyde, which is another major component of cinnamon, all of three different doses of cinnamaldehyde (10 mg/kg, 20 mg/kg, and 40 mg/kg, i.p.) did not have relief effects of oxaliplatin-induced cold allodynia and mechanical allodynia at all as compared with the cinnamic acid (FIG. 6).

(4) Test of Inhibitory Effect of Hyperexcitation of Spinal WDR Neurons Due to Cinnamic Acid In order to determine whether cinnamic acid may reduce the increased activity of WDR neurons occurring after oxaliplatin injection, extracellular recording was performed in the spinal cord of mice on the fourth day when the behavioral and electrophysiological correlation of neuropathic pain was established (FIG. 4). Cinnamic acid was administered intraperitoneally at a dose of 20 mg/kg, which was an optimal dose to attenuate cold allodynia and mechanical allodynia (FIG. 5), and DMSO (10%, i.p.) was used as a control. Mechanical (brush, press, and pinch) and cold (acetone drop) stimulations were applied before and after administration of the cinnamic acid or the control. The increased activity of the WDR neurons after oxaliplatin injection was significantly decreased after intraperitoneal administration of 20 mg/kg of cinnamic acid. However, 10% DMSO did not change the increased activity of WDR neurons (FIGS. 7A to 7D). Typical raw data were shown in FIG. 7E in which the hyperexcitation of WDR neurons for pinching and acetone drop was reduced by cinnamic acid. These results suggested that intraperitoneal administration of 20 mg/kg of cinnamic acid strongly inhibited the hyperexcitation of spinal WDR neurons in mice with cold allodynia and mechanical allodynia caused by oxaliplatin.

The results of Experimental Example 2 indicated that intraperitoneal administration of cinnamic acid could alleviate cold allodynia and mechanical allodynia induced by a single injection of oxaliplatin in mice. Moreover, this effect of cinnamic acid is associated with a decrease in hyperexcitation of spinal WDR neurons, which is increased by oxaliplatin treatment. Based on these results, it was suggested that cinnamic acid has a possibility of being an alternative to the current pain relievers used for the treatment of oxaliplatin-induced neuropathic pain.

Example 3—Preparation of Hot Water Extract of *Cinnamomi cortex* Containing Cinnamic Acid

*Cinnamomi cortex* from Vietnam (YB1), Indonesia (IN), and China (CN) was washed with distilled water, dried, and then finely ground with a grinder. 200 g of the ground sample was added with 2 L of distilled water and filtered after reflux extraction was repeated twice at 95° C. to 100° C. for 2 h. The filtered filtrate was concentrated under reduced pressure at 60° C. or lower, frozen in a cryogenic freezer, and freeze-dried with a freeze dryer to obtain the final extracts of YB1 28.44 g, IN 23.72 g, and CN 23.7 g.

As a result of analyzing the ingredients of each hot water extract of *Cinnamomi cortex* according to each production area, the result was as shown in Table 1 below.

TABLE 1

| | Major Compounds % extract (% material) | |
|---|---|---|
| Sample | Cinnamic acid | Cinnamaldehyde |
| YB1 (Vietnam) | 1.53 (0.109) | 0.27 (0.019) |
| IN (Indonesia) | 0.64 (0.038) | 0.02 (0.0012) |
| CN (China) | 0.93 (0.055) | 0.47 (0.028) |

Experimental Example 3—Test for Pain Relief when Hot Water Extract of *Cinnamomi cortex* was Administered in Anticancer Agent Pain Model Preparation of Animal Model 6-week-old mice (c57/bl6 mice) were prepared as an experimental animal, and allodynia was induced in the same manner as in the paclitaxel animal model of Experimental Example 1.

Experiment Schedule

From the 10th day when paclitaxel-induced allodynia was shown significantly, the hot water extract of each production area in Example 3 was administered orally for 5 consecutive days at 200 mg/kg, and then, according to the evaluation method of cold allodynia and mechanical allodynia of Experimental Example 1, it was confirmed whether allodynia was alleviated before administration (pre) and from day 2 to day 21 after administration.

Experiment Results

Figure 8:
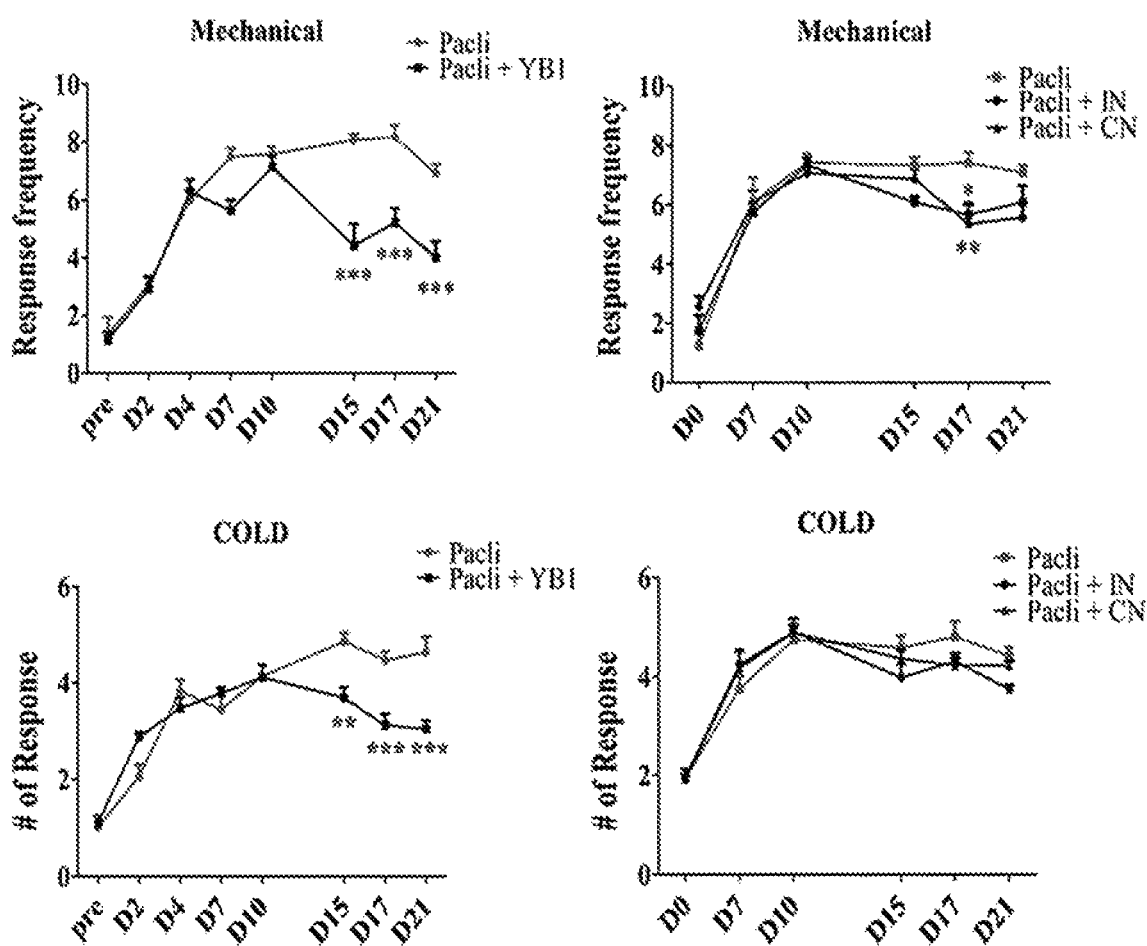
FIG. 8 is a diagram illustrating results of oral administration of a hot water extract of *Cinnamomi cortex* by production area containing cinnamic acid to an experimental animal group in which neuropathic pain is induced by a paclitaxel anticancer agent. YB1, IN, and CN represent *Cinnamomi cortex* from Vietnam, Indonesia, and China, respectively.

As a result of oral administration of 200 mg/kg of a hot water extract for each production area to an experimental animal group induced with neuropathic pain caused by paclitaxel, as illustrated in FIG. 8, YB1, originating from Vietnam, had a strong pain relief effect on mechanical allodynia and cold allodynia, and *Cinnamomi cortex* from other producing regions (CN from China, IN from Indonesia) had a temporary or weak pain relief effect.

As results of Experimental Example 3, it was showed that the hot water extract of *Cinnamomi cortex* from Vietnam with a high cinnamic acid content showed a superior pain relief effect compared to the hot water extract of *Cinnamomi cortex* from China/Indonesia with a lower cinnamic acid content, and it was suggested that cinnamic acid plays an important role in the reduction of mechanical allodynia and cold allodynia induced by paclitaxel.

In the present specification, detailed description has been omitted for those contents that can be sufficiently recognized and inferred by those skilled in the art of the present disclosure, and more various modifications are possible within the range that does not change the technical spirit or essential configuration of the present disclosure other than the specific examples described in the present specification. Therefore, the present disclosure may be implemented in a manner different from those specifically exemplified in the present specification, which can be understood by those skilled in the art of the present disclosure.

The invention claimed is:

1. A method for improving or treating cold allodynia caused by anticancer agents, comprising administering a composition consisting of cinnamic acid or a pharmaceutically acceptable salt thereof to a subject, wherein the anticancer agent is oxaliplatin, paclitaxel or vincristine.

2. A method of improving or treating mechanical allodynia caused by oxaliplatin, comprising administering a composition consisting of cinnamic acid or a pharmaceutically acceptable salt thereof to a subject.

3. The method of claim 1 or 2, wherein the pharmaceutical composition is administered orally or injected intraperitoneally in an amount of 5 mg/kg to 100 mg/kg.

4. The method of claim 1 or 2, wherein the composition is a food composition.

5. The method of claim 1 or 2, wherein the composition is a pharmaceutical composition.

6. A method for improving or treating allodynia caused by anticancer agents, comprising administering a composition consisting of a water extract of *Cinnamomi cortex* from Vietnam to a subject,
wherein the allodynia is cold allodynia or mechanical allodynia, and
wherein the anticancer agent is paclitaxel, and
wherein the water extract of *Cinnamomi cortex* from Vietnam comprises 1% to 3% cinnamic acid or a pharmaceutically acceptable salt thereof.

7. The method of claim 6, wherein the composition is administered orally in an amount of 50 mg/kg to 500 mg/kg.

8. The method of claim 6, wherein the composition is a food composition.

9. The method of claim 6, wherein the composition is a pharmaceutical composition.

* * * * *